(12) United States Patent
Lasko

(10) Patent No.: US 6,497,688 B2
(45) Date of Patent: *Dec. 24, 2002

(54) ABSORBENT ARTICLE COMPRISING FLOCKED FIBERS

(75) Inventor: Vincent P. Lasko, New Egypt, NJ (US)

(73) Assignee: McNeil-PPC, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/356,947

(22) Filed: Jul. 19, 1999

(65) Prior Publication Data
US 2002/0013561 A1 Jan. 31, 2002

(51) Int. Cl.$^7$ ................................................ A61F 13/16
(52) U.S. Cl. ........................................ 604/367; 604/358
(58) Field of Search ................................ 604/354, 364, 604/365, 367, 378, 384–387, 385.01, 385.03, 385.23

(56) References Cited

U.S. PATENT DOCUMENTS

| | | | | |
|---|---|---|---|---|
| 2,527,501 A | * | 10/1950 | Saks | |
| 2,691,611 A | * | 10/1954 | Saks | |
| 3,436,442 A | * | 4/1969 | Saks | |
| 3,672,929 A | * | 6/1972 | Riordan | |
| 3,967,623 A | * | 7/1976 | Butterworth | 128/287 |
| 4,054,141 A | * | 10/1977 | Schwaiger et al. | 128/287 |
| 4,324,246 A | | 4/1982 | Mullane et al. | |
| 4,459,332 A | | 7/1984 | Giglia | |
| 4,681,578 A | * | 7/1987 | Anderson et al. | 604/385 R |
| 4,826,498 A | * | 5/1989 | Koczab | 604/383 |
| 5,002,814 A | * | 3/1991 | Knack et al. | 428/85 |
| 5,843,064 A | * | 12/1998 | Koczab | 604/378 |
| 5,885,268 A | * | 3/1999 | Bien et al. | 604/385.1 |
| 6,365,794 B1 | * | 4/2002 | Dabi et al. | 604/367 |

FOREIGN PATENT DOCUMENTS

| | | |
|---|---|---|
| BE | 1 007 041 A | 2/1995 |
| DE | 32 14 354 A | 10/1983 |
| DE | 93 07 894 A | 5/1993 |
| EP | 0 374 910 A | 6/1990 |
| EP | 0 661 030 A | 7/1995 |
| EP | 00 737 462 A1 * | 10/1996 |
| EP | 0 861 646 A | 9/1998 |
| EP | 0 976 375 A | 2/2000 |
| EP | 1 070 492 A | 1/2001 |
| WO | WO 94/05244 A | 3/1994 |
| WO | 95/13773 * | 11/1994 |
| WO | WO 97/34507 A | 9/1997 |
| WO | WO 98/25560 A | 6/1998 |

OTHER PUBLICATIONS

European Search Report (ApplicationNo. EP 00 11 5482); Completion date: Apr. 3, 2001.
Pamphlet, *Design with Flock in Mind*™, published by the American Flock Association of Boston, Massachusetts.
Dr. F. Masuda; "The concept of superabsorbent polymer"; presented as paper No. 13 @ The Pira Fibramerics Programme held Dec. 1–3, 1987.

* cited by examiner

Primary Examiner—John G. Weiss

(57) ABSTRACT

An absorbent article is provided comprising flocked fibers adhered to one or more internal surfaces of an absorbent article comprising a cover, an absorbent core, and a backsheet, such as the internal surface of the cover, either surface of the absorbent core, or the internal surface of the backsheet.

12 Claims, 2 Drawing Sheets

ABSORBENT ARTICLE COMPRISING FLOCKED FIBERS

The present invention relates to an absorbent article, such as a sanitary napkin or pantiliner comprising a cover, an absorbent core, and a backsheet. The absorbent article comprises flocked fibers adhered to an internal surface of the absorbent article, such as the absorbent core-facing surface of the cover, either surface of the absorbent core, or the absorbent core-facing surface of the backsheet.

BACKGROUND OF THE INVENTION

Absorbent articles may take many forms, such as sanitary napkins, pantiliners, diapers, incontinence pads, and interlabial articles. In such articles, it is often desirable to incorporate fibers for a variety of purposes. For example, fibers of superabsorbent polymer may be added to increase the absorbency of the articles. Unfortunately, fibers of superabsorbent polymers are often brittle and it is usually difficult to incorporate fibers of superabsorbent polymers into absorbent articles using known manufacturing techniques. In particular, when fibers of superabsorbent polymers are dispersed into an air laid-type matrix using special handling equipment, they become compressed by adjacent superabsorbent polymer fibers and other fibers in the matrix. When compressed, fibers of superabsorbent polymer cannot fully swell as they absorb fluids, and their absorbent capacity is underutilized.

Flocking is a technique by which fibers are fixed in a vertical position on a substrate, and is primarily used in the fabric industry. However, EP 0 737 462 A1 discloses a laminated material to cover the outside of an absorbent product, characterized in that at least one portion of the surface of the laminated material bears a layer of fibers applied by flocking. The flocked fibers are thereby located on the external surface of the absorbent product in order to give the absorbent product improved tactile properties over products that employ plastic films against the skin.

Applicant has now discovered that flocked fibers may advantageously be applied to one or more of the internal surfaces of an absorbent article. In an absorbent article comprising a cover, an absorbent core, and a backsheet, for example, the flocked fibers may be applied to the absorbent core-facing surface of the cover, the cover-facing surface of the absorbent core, the backsheet-facing surface of the absorbent core, or the absorbent core-facing surface of the backsheet. The fibers are preferably selected from superabsorbent polymers and other hydrophilic materials, hydrophobic materials, and mixtures thereof, so as to provide an absorbent article with improved absorbent capacity and physical integrity.

SUMMARY OF THE INVENTION

The present invention provides an absorbent article having a body-facing surface and a garment-facing surface and comprising in sequence a cover, an absorbent core, and a backsheet, wherein the absorbent article comprises flocked fibers, said flocked fibers not being adhered to the body-facing surface or the garment-facing surface of the absorbent article.

DETAILED DESCRIPTION OF THE INVENTION

The absorbent article may for example be a sanitary napkin, a pantiliner, a diaper, incontinence pad, interlabial article, or other similar product for absorbing exudates from the body, such as menses, urine, or feces. Preferably, the absorbent article is a sanitary napkin or a pantiliner. Such sanitary napkin or pantiliner may have an approximately rectangular, oval, dogbone, or peanut shape. Depending on the nature of the absorbent article, its size may vary. For example, sanitary napkins typically have a caliper of about 1.4 to about 5 mm, a length of about 3 to about 16 inches, and a width of about 1 to about 5 inches. Pantiliners typically have a caliper of less than about 0.2 inches, a length of less than about 8 inches, and a width of less than about 3 inches.

Figure 1:
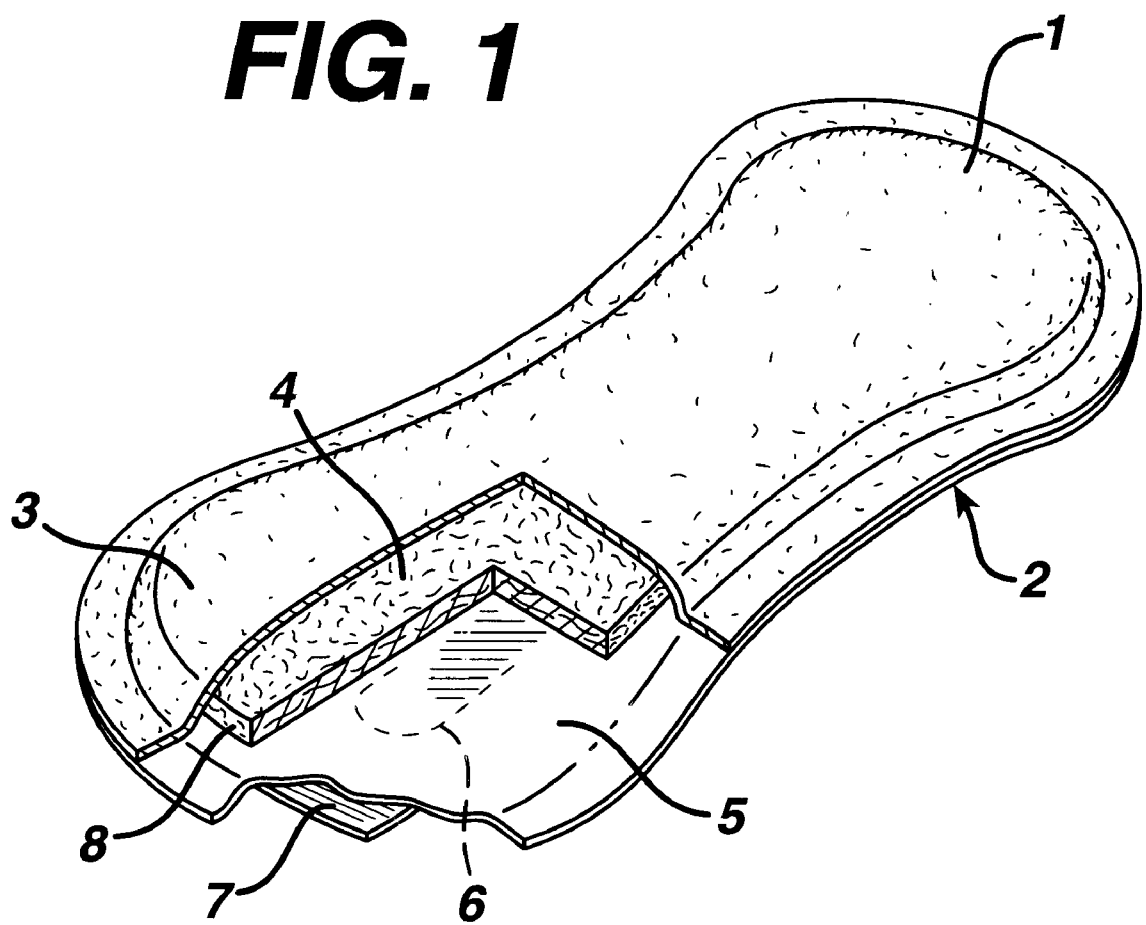
FIG. 1 depicts an absorbent article (pantiliner) according to the invention.

FIG. 1 depicts such a pantiliner according to the invention, and is used for purposes of illustration in the following description. The pantiliner shown in FIG. 1 comprises in sequence from its body-facing surface 1 to its garment-facing surface 2 liquid permeable cover 3, an absorbent core 4, and a liquid impermeable backsheet 5. The cover 3 of the absorbent article may be formed from any fluid pervious material that is comfortable against the skin and permits fluid to penetrate to the absorbent core, which retains the fluid. The cover should retain little or no fluid to provide a relatively dry surface, since its external surface forms the body-facing surface 1 of the article. A variety of materials are known for preparing covers, and any of these may be used. For instance, the cover may be a fibrous non-woven fabric made of fibers or filaments of polymers such as polyethylene, polypropylene, polyester, or cellulose. Alternatively, the cover may be formed from an apertured polymeric film. The thickness of the cover may vary from approximately 0.001 to 0.062 inch, depending on the material chosen.

Generally, cover 3 is a single sheet of material having a width sufficient to form the body-facing surface 1 of the article. The cover may be the same length, or optionally longer than the absorbent core so as to form transverse ends. Such transverse ends may be sealed with other layers to fully enclose the absorbent core.

The absorbent core 4 may be comprised of a loosely associated absorbent hydrophilic material such as cellulose fibers, including wood pulp, regenerated cellulose fibers or cotton fibers, or other absorbent materials generally known in the art, including acrylic fibers, polyvinyl alcohol fibers, peat moss and superabsorbent polymers.

The absorbent article further comprises a liquid impermeable backsheet 5, the exterior of which forms the garment-facing surface 2 of the article. The backsheet may comprise any thin, flexible, body fluid impermeable material such as a polymeric film, for example, polyethylene, polypropylene, or cellophane. Alternatively, the backsheet may be a normally fluid permeable material that has been treated to be impermeable, such as impregnated fluid repellent paper or non-woven fabric material, or a flexible foam, such as polyurethane or cross-linked polyethylene. The thickness of the backsheet when formed from a polymeric film typically is about 0.001 to 0.002 inch. A variety of materials are known in the art for use as backsheet, and any of these may be used.

Generally, the backsheet 5 is a single sheet of material having a width sufficient to form the garment-facing surface 2 of the absorbent article. The backsheet may extend around the sides of the absorbent core in a C-shaped configuration with the portions of the backsheet adjacent its longitudinal edges extending upwardly from the garment-facing surface toward the body-facing surface of the article. Preferably the backsheet is breathable, i.e., a film that is a barrier to liquids but permits gases to transpire. Materials for this purpose include polyurethane films and microporous films in which microporosity is created by ionizing radiation or by leaching out of soluble inclusions using aqueous or nonaqueous solvents. Single or multiple layers of permeable films, fabrics, and combinations thereof that provide a tortuous path, and/or whose surface characteristics provide a liquid surface repellent to the penetration of liquids may also be used to provide a breathable backsheet.

The absorbent article may be applied to the crotch of underpants by placing the garment-facing surface 2 of the absorbent article against the inside surface of the crotch of the underpants. Strips of pressure sensitive adhesive 6 may be applied to the garment-facing surface 2 of the absorbent article to help maintain it in place. As used herein, the term "pressure-sensitive adhesive" refers to any releasable adhesive or releasable tenacious means. Suitable pressure sensitive adhesives include for example water-based adhesives such as acrylate adhesives. Alternatively, the adhesive may comprise rapid setting thermoplastic "hot melt" rubber adhesives or two-sided adhesive tape.

A paper release strip 7 that has been coated on one side may be applied to protect the strips of adhesive 6 prior to use. The coating, for example silicone, reduces adherence of the coated side of the release strip to the adhesive. The release strip can be formed from any suitable sheet-like material which, when coated, adheres with sufficient tenacity to the adhesive to remain in place prior to use but can be readily removed when the absorbent article is to be used.

The absorbent article may comprise other known materials, layers, and additives, such as transfer layers, foam layers, net-like layers, odor control agents, perfumes, medicaments, moisturizers, and the like, many examples of which are known in the art. A transfer layer in particular, however, may advantageously be unnecessary in the present absorbent article, as further explained below. The absorbent article can optionally be embossed with decorative designs using conventional techniques.

According to the invention, the absorbent article comprises flocked fibers on one or more internal surfaces. The flocked fibers may be hydrophilic, hydrophobic, or a combination of the two. Hydrophilic fibers include wettable fibers, i.e., hydrophobic fibers that have been treated with a wetting agent to render them hydrophilic, absorbent fibers, and superabsorbent polymer fibers. Examples of wettable fibers include bicomponent fibers, polypropylene fibers, and polyester fibers that have been treated for example with surfactants. Preferred wettable fibers are polyester fibers, such as DuPont-Akra Polyester Type 11A Bright commercially available from DuPont Company treated with a surfactant such as Tween 20 commercially available from ICI Americas Inc.

Absorbent fibers are hydrophilic fibers that both that have an affinity for and absorb fluids. Absorbent fibers may comprise rayon fibers, acrylic fibers, nylon fibers, polyvinyl alcohol fibers, and fibers of natural or regenerated cellulosics. A preferred type of absorbent fiber is rayon fibers.

Superabsorbent polymer fibers are hydrophilic fibers that are swellable and capable of absorbing greater than about 5 grams per gram (of fiber weight) of 1% saline solution. Examples of superabsorbent polymer fibers are polyacrylate fibers, fibers of grafted cellulose, and fibers of maleic acid. Preferred types of superabsorbent polymer fibers include OASIS Type 101, commercially available from Technical Absorbents Limited and CAMELOT, commercially available from Camelot, Alberta, Canada.

Hydrophobic fibers include certain olefin fibers and large denier polyester fibers, preferably having a denier of at least 3, more preferably at least 6. A preferred hydrophobic fiber is 15 denier polyester commercially available from DuPont Company.

Regardless of type, the length of the flocked fibers should be less than about 1 mm, preferably less than about 0.8 mm. The denier of the flocked fibers should be in the range of about 1.2d to about 15d, preferably about 1.8d to about 6d. It is also preferred that the fibers suffer little or no wet collapse.

The flocked fibers may be adhered to all or a portion of any internal surface inside the absorbent article. This includes the absorbent core-facing surface of the cover, the cover-facing surface of the absorbent core, the backsheet-facing surface of the absorbent core, or the absorbent core-facing surface of the backsheet. In FIG. 1, flocked superabsorbent polymer fibers 8 are adhered to the cover-facing surface of the absorbent core. The flocked fibers may be on one or both sides of a particular layer in the absorbent article. The same or different flocked fibers may be on two or more different internal surfaces. The flocked fibers may also be adhered to the surface of any other internal layer optionally used in the absorbent article, such as transfer layers, net-like layers, additional absorbent layers, and the like.

Methods of flocking fibers onto a surface are known in the art of fabric manufacture. See for example, U.S. Pat. Nos. 2,527,501; 2,691,611; 3,436,442; and 3,672,929. Typically, a substrate, such as a cover, is coated with adhesive on all or a portion of its surface. The coated substrate is then passed through a fiber metering station in which an electrostatic field is maintained around the substrate, using for example electrodes situated above and below the substrate. The fibers are applied to the adhesive on the substrate in the presence of the electrostatic field, which orients the fibers perpendicular to the substrate as they contact the adhesive. The substrate is then heated, polymerizing the adhesive and anchoring the fibers. Unattached fibers may be vacuumed away.

Preferably, the adhesive employed to attach the fibers to the internal surface is a polymerizable resin, such as modified acrylic water based compounds, for example FLEXBOND 974, 977, 983, and 986 commercially available from Air Products, CARBOTAC Adhesives (PSAs) commercially available from BF Goodrich, and CARBOBOND Adhesives (non-PSAs) also commercially available from BF Goodrich.

Figure 2:
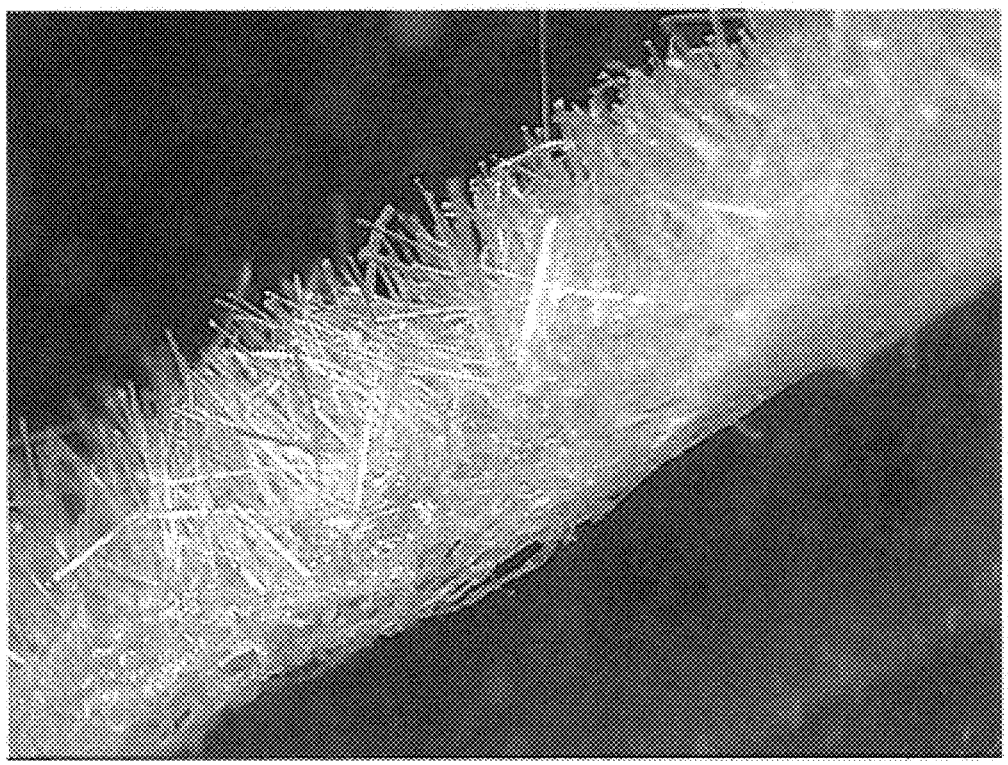
FIG. 2 is an magnified view of an absorbent core with flocked fibers adhered to the surface thereof according to the invention.

FIG. 2 is an enlarged photograph of an air laid pulp material commonly used as an absorbent core in absorbent products. It comprises flocked fibers of superabsorbent polymer, rayon, and polyester.

In one particularly preferred embodiment of the invention, the flocked fibers comprise one or more type of superabsorbent polymer fibers. Superabsorbent polymers, in the form of both particles and fibers, are known to increase the liquid management properties of absorbent articles, such as capacity and retention of fluids. However, according to the invention, when flocked fibers of superabsorbent polymer are applied to a substrate, they stand in an upright, vertical manner on the surface. Such an orientation allows the flocked fibers of superabsorbent polymer to absorb an increased amount of fluid compared with unflocked fibers of superabsorbent polymer, i.e., fibers compressed horizontally.

Preferably, flocked superabsorbent polymer fibers are adhered to the cover-facing surface of the absorbent core. Superabsorbent polymer fibers adhered to the cover-facing surface of the absorbent core draw fluid efficiently into the absorbent core. If desired, the absorbent core may be densified in accordance with this embodiment, so as to provide lateral wicking of the fluid once it enters the absorbent core.

The overall amount of superabsorbent polymer contained by the absorbent article may range from about 0.1 to about 5 grams, preferably from about 0.2 to about 2.5 grams, more preferably from about 0.3 to about 1 grams. Of this, up to 100 percent may be in the form of flocked fibers. The remainder, if any, is contained in the absorbent core as particles, fibers, or both.

In another embodiment of the invention, the flocked fibers comprise a combination of superabsorbent polymer fibers and other hydrophilic fibers (i.e., wettable fibers, absorbent fibers, or both). In this embodiment, fluid is quickly absorbed by the other hydrophilic fibers and then transferred to the superabsorbent polymer fibers. Although the superabsorbent polymer fibers absorb more slowly than the other hydrophilic fibers, the superabsorbent polymer fibers have overall higher capacity and increased fluid retention.

In this embodiment, the amount of superabsorbent polymer in the combined superabsorbent polymer fibers/other hydrophilic fibers is typically from about 5 to about 95 percent by weight, preferably from about 30 to about 70 percent by weight. The flocked superabsorbent polymer fibers may be uniformly dispersed in the other hydrophilic fibers, or the superabsorbent polymer fibers and other hydrophilic fibers may be adhered to the internal surface in patterns.

In a particularly preferred embodiment of the invention, the flocked fibers comprise a combination of superabsorbent polymer fibers, other hydrophilic fibers, and hydrophobic fibers. Again, fluid is quickly absorbed by the other hydrophilic fibers and transferred to the higher fluid capacity superabsorbent polymer fibers. The hydrophobic fibers absorb little or no fluid and therefore advantageously maintain their physical integrity, such as to minimize wet collapse. The hydrophobic fibers support the superabsorbent polymer fibers and other hydrophilic fibers as the latter absorb fluid and lose their rigidity. Moreover, due to the upright support of the hydrophobic fibers, less pressure is placed on the internal layers of the absorbent article, also increasing the absorbent capacity of the absorbent article. In this manner, the overall structure and physical integrity of the absorbent article is preserved.

The use of flocked hydrophobic fibers in an absorbent article has the additional advantage of disposing with the need for a transfer layer or second cover layer often used, for example, in sanitary napkins. Transfer layers are typically hydrophobic and are located between the cover and the absorbent core of an absorbent article. They separate the absorbent core from external pressure placed on the absorbent article during use. This function may be fulfilled by the flocked hydrophobic fibers in an thinner and simpler construction. Moreover, flocked hydrophobic fibers exert less pressure on the absorbent core than a transfer layer, since the former are oriented perpendicular to the surface of the absorbent core.

In this embodiment, the amount of superabsorbent polymer in the combined superabsorbent polymer fibers/other hydrophilic fibers/hydrophobic fibers is typically from about 5 to about 95 percent by weight, preferably from about 30 to about 70 percent by weight. The superabsorbent polymer fibers may be uniformly dispersed in the other hydrophilic fibers hydrophobic fibers, or the various fibers may be adhered to the internal surface in patterns.

The following non-limiting examples further illustrate the invention.

EXAMPLE 1

An absorbent core comprising flocked fibers of superabsorbent polymer was prepared as follows.

A one ounce per square yard substrate of 100% polyester was used as the carrier fabric. A polymerizable resin was applied in various patterns to the polyester fabric. A fiber blend consisting of 30 percent superabsorbent polymer fibers, 40 percent rayon fibers, and 30 percent polyester fibers was metered on the polyester fabric. The fibers were oriented in the vertical position via an electrostatic field. The fibers adhered where the resin was applied. The substrate was then passed through an oven to polymerize the resin, anchoring the fibers to the polyester fabric. The excess fibers were vacuumed away.

EXAMPLE 2

The absorbent core of Example 1 is used to make a pantiliner as follows. A fluid permeable, nonwoven cover is placed over the absorbent core, with the surface of the absorbent core containing the flocked fibers facing the cover. A fluid impermeable backsheet is positioned underneath the absorbent core on the surface of the absorbent core that does not contain flocked fibers.

I claim:

1. An absorbent article comprising in sequence a cover having a body-facing surface, an absorbent core, and a backsheet having a garment-facing surface, wherein the absorbent article further comprises flocked fibers wherein said flocked fibers comprise superabsorbent polymer fibers and said flocked fibers not being adhered to the body-facing surface of the cover and the garment-facing surface of the backsheet.

2. The absorbent article of claim 1, wherein the fibers are adhered to the cover on its absorbent core-facing surface.

3. The absorbent article of claim 1, wherein the fibers are adhered to the absorbent core on its cover-facing surface.

4. The absorbent article of claim 1, wherein the fibers are adhered to the absorbent core on its backsheet-facing surface.

5. The absorbent article of claim 1, wherein the fibers are adhered to the backsheet on its absorbent core-facing surface.

6. The absorbent article of claim 5, wherein the backsheet is breathable.

7. The absorbent article of claim 1, wherein the fibers comprise hydrophilic fibers.

8. The absorbent article of claim 7, wherein the hydrophilic fibers are selected from the group consisting of wettable fibers, absorbent fibers, and mixtures thereof.

9. The absorbent article of claim 8, wherein the fibers comprise a combination of wettable fibers, absorbent fibers, and superabsorbent polymer fibers.

10. The absorbent article of claim 1, wherein the fibers further comprise hydrophobic fibers.

11. The absorbent article of claim 10, wherein the fibers further comprise a combination of hydrophilic fibers.

12. The absorbent article of claim 11, wherein the hydrophilic fibers are selected from the group consisting of wettable fibers, absorbent fibers, and mixtures thereof.

* * * * *